(12) United States Patent  
Nigg et al.

(10) Patent No.: US 11,624,523 B2  
(45) Date of Patent: Apr. 11, 2023

(54) SYSTEM AND METHOD FOR REMOTE CALIBRATION OF AN AIR-QUALITY SENSOR DEVICE

(71) Applicant: Integrated Energy Services Corporation, New York, NY (US)

(72) Inventors: Brock L. Nigg, Darien, CT (US); Steve Schlanger, Flagstaff, AZ (US); Frank Ableson, Stanhope, NJ (US)

(73) Assignee: INTEGRATED ENERGY SERVICES CORPORATION, New York, NY (US)

( * ) Notice: Subject to any disclaimer, the term of this patent is extended or adjusted under 35 U.S.C. 154(b) by 138 days.

(21) Appl. No.: 17/017,302

(22) Filed: Sep. 10, 2020

(65) Prior Publication Data  
US 2021/0072206 A1 Mar. 11, 2021

Related U.S. Application Data

(60) Provisional application No. 62/898,248, filed on Sep. 10, 2019.

(51) Int. Cl.  
*G01N 33/00* (2006.01)  
*F24F 11/46* (2018.01)  
(Continued)

(52) U.S. Cl.  
CPC .............. *F24F 11/46* (2018.01); *F24F 11/39* (2018.01); *F24F 11/47* (2018.01); *F24F 11/52* (2018.01);  
(Continued)

(58) Field of Classification Search  
CPC ...... H04W 52/0206; F24F 11/46; F24F 11/39; F24F 11/58; F24F 11/63; F24F 2110/50;  
(Continued)

(56) References Cited

U.S. PATENT DOCUMENTS 4,481,596 A 11/1984 Townzen  
4,532,013 A 7/1985 Dietz et al.  
(Continued)

FOREIGN PATENT DOCUMENTS

| CN | 109028510 A | 12/2018 | |
|---|---|---|---|
| EP | 3270118 A1 * | 1/2018 | ........... F01D 21/003 |
| RU | 2439442 C1 | 1/2012 | |

OTHER PUBLICATIONS

Hagan et al., "Calibration and Assessment of Electrochemical Air Quality Sensors by Co-Location with Regulatory-Grade Instruments", Atmospheric Measurement Techniques, 2018, pp. 315-328.  
(Continued)

*Primary Examiner* — Jeffrey P Aiello  
(74) *Attorney, Agent, or Firm* — M&B IP Analysts, LLC (57) ABSTRACT

A system and method for remote calibration of an air-quality sensor device. The method includes receiving sensor data from at least one sensor device; analyzing the received sensor data to identify at least statistically-significant values indicating on at least drift from initial calibrated values of each of the at least one sensor device; for each identified drifted sensor device, computing re-calibration updates, wherein the re-calibration updates adjust the initial calibrated values such that readings of the respective drifted sensor device fall within a range of expected values; and transmitting the re-calibration updates to the respective drifted sensor device, wherein the respective drifted sensor device upon receiving the re-calibration updates is configured to update its calibration parameters.

25 Claims, 6 Drawing Sheets

(51) Int. Cl.
| | |
|---|---|
| *F24F 11/58* | (2018.01) |
| *F24F 11/52* | (2018.01) |
| *F24F 11/63* | (2018.01) |
| *H04W 52/02* | (2009.01) |
| *F24F 11/39* | (2018.01) |
| *F24F 11/47* | (2018.01) |
| *G08C 17/02* | (2006.01) |
| *F24F 110/50* | (2018.01) |
| *F24F 110/20* | (2018.01) |
| *F24F 140/60* | (2018.01) |
| *F24F 110/70* | (2018.01) |
| *F24F 110/74* | (2018.01) |
| *F24F 110/40* | (2018.01) |
| *F24F 110/66* | (2018.01) |
| *F24F 110/10* | (2018.01) |

(52) U.S. Cl.
CPC .............. *F24F 11/58* (2018.01); *F24F 11/63* (2018.01); *G01N 33/0006* (2013.01); *G01N 33/0073* (2013.01); *G01N 33/0075* (2013.01); *G08C 17/02* (2013.01); *H04W 52/0206* (2013.01); *H04W 52/0235* (2013.01); *F24F 2110/10* (2018.01); *F24F 2110/20* (2018.01); *F24F 2110/40* (2018.01); *F24F 2110/50* (2018.01); *F24F 2110/66* (2018.01); *F24F 2110/70* (2018.01); *F24F 2110/74* (2018.01); *F24F 2140/60* (2018.01); *G08C 2201/12* (2013.01); *G08C 2201/40* (2013.01)

(58) Field of Classification Search
CPC .............. F24F 2110/66; F24F 2110/70; F24F 2110/74; G01N 33/0006; G01N 33/0073; G01N 33/0075; G08C 17/02
USPC ........... 73/23.2; 340/632; 700/1; 702/24, 27, 702/81, 104, 127, 179, 182, 187–189
See application file for complete search history.

(56) References Cited

U.S. PATENT DOCUMENTS

| | | | |
|---|---|---|---|
| 4,858,615 A | 8/1989 | Meinema | |
| 5,016,198 A * | 5/1991 | Schreiber | G01D 3/022 73/114.61 |
| 5,321,638 A | 6/1994 | Witney | |
| 5,498,872 A | 3/1996 | Stedman et al. | |
| 6,581,435 B2 | 6/2003 | Wang et al. | |
| 6,903,330 B2 | 6/2005 | Evans et al. | |
| 6,908,224 B2 | 6/2005 | Schneider et al. | |
| 7,571,065 B2 | 8/2009 | Seesink | |
| 7,599,815 B2 * | 10/2009 | Reichel | F24F 11/30 702/182 |
| 8,428,909 B2 * | 4/2013 | Collins | G01F 25/10 702/179 |
| 8,682,937 B2 | 3/2014 | Ludwig | |
| 9,213,016 B1 * | 12/2015 | Stetter | G01N 33/0006 |
| 9,756,403 B2 | 9/2017 | Proud | |
| 10,349,873 B2 | 7/2019 | Kamath et al. | |
| 10,687,231 B1 | 6/2020 | Stamatakis | |
| 10,712,264 B2 | 7/2020 | Carbonelli et al. | |
| 10,724,976 B2 | 7/2020 | Rogers et al. | |
| 10,758,665 B2 | 9/2020 | Igarashi et al. | |
| 10,827,980 B2 | 11/2020 | Shariati et al. | |
| 11,141,549 B2 | 10/2021 | Tolmie et al. | |
| 11,346,554 B2 | 5/2022 | Shuk et al. | |
| 2003/0080288 A1 | 5/2003 | Evans et al. | |
| 2003/0145644 A1 | 8/2003 | Rabbett et al. | |
| 2007/0242688 A1 | 10/2007 | McFarland | |
| 2009/0012738 A1 | 1/2009 | Hart et al. | |
| 2010/0081411 A1 | 4/2010 | Montenero | |
| 2010/0177750 A1 * | 7/2010 | Essinger | H04L 67/12 345/522 |
| 2011/0074552 A1 | 3/2011 | Norair et al. | |
| 2012/0242453 A1 | 9/2012 | Delgado et al. | |
| 2012/0277566 A1 | 11/2012 | Kamath | |
| 2012/0303164 A1 * | 11/2012 | Smith | H05K 7/20836 700/276 |
| 2013/0038470 A1 | 2/2013 | Niemeyer et al. | |
| 2013/0174646 A1 * | 7/2013 | Martin | F24F 11/62 73/31.02 |
| 2013/0298642 A1 * | 11/2013 | Gillette, II | G01J 5/025 73/31.01 |
| 2014/0009268 A1 | 1/2014 | Oshima et al. | |
| 2014/0037506 A1 | 2/2014 | Miki et al. | |
| 2014/0053586 A1 * | 2/2014 | Poecher | F24F 11/83 73/28.01 |
| 2014/0126382 A1 | 5/2014 | Tian et al. | |
| 2014/0129004 A1 | 5/2014 | Takayama et al. | |
| 2014/0247140 A1 * | 9/2014 | Proud | A61B 5/02055 340/870.02 |
| 2015/0057960 A1 * | 2/2015 | Dupont De Dinechin | G01B 21/00 702/182 |
| 2015/0096352 A1 * | 4/2015 | Peterson | G08B 25/012 73/31.02 |
| 2015/0195780 A1 | 7/2015 | Liu | |
| 2015/0285755 A1 * | 10/2015 | Moss | G01N 27/121 702/133 |
| 2016/0116181 A1 | 4/2016 | Quitman et al. | |
| 2016/0135242 A1 | 5/2016 | Hampel et al. | |
| 2016/0255697 A1 | 9/2016 | Bhide | |
| 2016/0360300 A1 | 12/2016 | Proud | |
| 2018/0120279 A1 * | 5/2018 | Yi | G01N 33/0075 |
| 2018/0156484 A1 | 6/2018 | Kim et al. | |
| 2018/0356809 A1 * | 12/2018 | Trainor | G05B 23/0229 |
| 2019/0012903 A1 * | 1/2019 | Cai | G08B 29/20 |
| 2020/0003447 A1 | 1/2020 | Lee et al. | |
| 2020/0300756 A1 | 9/2020 | Carbonelli et al. | |
| 2020/0316282 A1 | 10/2020 | Igarashi | |
| 2020/0393152 A1 | 12/2020 | Ramirez et al. | |
| 2021/0041125 A1 | 2/2021 | Liu et al. | |
| 2021/0058826 A1 | 2/2021 | Mao et al. | |
| 2022/0003581 A1 | 1/2022 | Fox et al. | |

OTHER PUBLICATIONS

International Search Report and Written Opinion of International Searching Authority for PCT/US2020/050198, ISA/RU, Moscow, Russia, dated Nov. 13, 2020.
International Search Report and Written Opinion of International Searching Authority for PCT/US2020/048472, ISA/RU, Moscow, Russia, dated Nov. 19, 2020.
International Search Report and Written Opinion of International Searching Authority for PCT/US2020/049934, Isa/Ru, Moscow, Russia, dated Nov. 11, 2020.
International Search Report and Written Opinion of International Searching Authority for PCT/US2020/049937, ISA/RU, Moscow, Russia, dated Nov. 26, 2020.
Vaquerizo-Hdez et al., "A Low Power Consumption Algorithm for Efficient Energy Consumption in ZigBee Motes", ntelligent Systems Group, Computer Engineering Department, Universidad de Alcala; Sensors: MDPI, Aug. 19, 2017.
GasAlertMicro 5 02, CO, H2S, PH3, SO2, Cl2, NH3, NO2, HCN, ClO2, 03, VOC, and Combustibles 1, 2, 3, 4, and 5 Gas Detectors User Manual, BW Technologies, Copyright 2005, available online at least as early as May 15, 2008. (Year: 2008).
Partial File Directory from JJS Technical Services, Inc. Listing Document Uploads at least as early as May 15, 2008.

* cited by examiner

SYSTEM AND METHOD FOR REMOTE CALIBRATION OF AN AIR-QUALITY SENSOR DEVICE

CROSS-REFERENCE TO RELATED APPLICATIONS

This application claims the benefit of U.S. Provisional Application No. 62/898,248 filed on Sep. 10, 2019, the contents of which are hereby incorporated by reference.

TECHNICAL FIELD

The present disclosure relates generally to air quality assurance and energy management and, more particularly, to systems and methods for calibration of devices for environmental monitoring, advisement, and control of commercial and industrial buildings.

BACKGROUND

While certain improvements in building materials, construction techniques, and electronic systems provide for improved efficiency in operation of a building, energy costs remain among a building operator's greatest expenses. Energy costs, such as those costs arising from heating or cooling a building, may vary greatly based on factors such as resident or tenant environmental preferences, demand-based energy pricing, environmental conditions, and the like. Further, building operators may wish to provide for building air quality management and the comfort of tenants and residents, in addition to cost-optimization, creating a complex balance of energy costs and building requirements, a balance which legacy systems may be ill-equipped to resolve.

Legacy building management systems may provide for the collection of data relating to building environmental conditions. Further, such legacy systems may include features providing for control of building conditions using devices such as thermostat-linked heating and cooling systems, remote shutoffs for conduits, and the like. While such legacy systems may provide for environmental control and data collection, legacy means may be ill-suited to high-volume data processing and may lack certain connectivity features useful in reducing operator workload and maintenance.

In addition to the inefficiencies of legacy systems in managing high-volume building data, such systems may fail to provide certain modern functionalities necessary for efficient building environmental system management. Legacy systems may lack cloud-processing systems which provide for collection and analysis of large volumes of building data. Further, legacy systems may lack the interconnectivity required to collect energy market and grid data and to respond to such data automatically. In addition, legacy systems may require manual calibration and re-calibration of sensor and regulator devices, where manual calibration and re-calibration may require a prohibitively large outlay of time and effort on the part of building management and maintenance teams.

Further, legacy systems may fail to provide for management of building wellness controls. Building wellness controls include those controls concerning health and wellness parameters of building management, such as air filter status, air quality status, and the like, as opposed to comfort controls which may be directed to provision of comfortable conditions for building occupants, such as controls directed to air temperatures. Further, legacy systems may require various trade-offs between wellness, comfort, and energy efficiency to reach various building management goals. As a result, legacy systems may lack the capacity to provide optimized wellness, comfort, and energy solutions, requiring intensive manual adjustment of wellness, comfort, and energy parameters to reach desired building control states.

In addition to legacy building management systems, certain smaller-scale comfort and energy management systems may provide similar functionalities in smaller-scope applications, such as homes, small offices, and the like. Examples of smaller-scale comfort and energy management systems include the Nest® home management system by Google®. While smaller-scale systems provide for certain energy and comfort control functionalities, such systems lack the scope of application required to provide centrally-managed control of wellness, comfort, and energy needs for larger buildings such as office towers, retail stores, and the like, as such buildings may include large numbers of management devices, complex connectivity architectures, predefined communication protocols, and the like. Further, smaller-scale systems may be primarily directed to management of comfort and energy parameters, to the exclusion of integrated safety and wellness controls. As a result, smaller-scale management systems may fail to provide functionalities and scopes of application required for use in large-scale building systems management applications.

It would therefore be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for remote calibration of an air-quality sensor device. The method comprises receiving sensor data from at least one sensor device; analyzing the received sensor data to identify at least statistically-significant values indicating on at least drift from initial calibrated values of each of the at least one sensor device; for each identified drifted sensor device, computing re-calibration updates, wherein the re-calibration updates adjust the initial calibrated values such that readings of the respective drifted sensor device fall within a range of expected values; and transmitting the re-calibration updates to the respective drifted sensor device, wherein the respective drifted sensor device upon receiving the re-calibration updates is configured to update its calibration parameters.

Certain embodiments disclosed herein also include a non-transitory computer readable medium having stored thereon causing a processing circuitry to execute a process, the process comprising: receiving sensor data from at least one sensor device; analyzing the received sensor data to identify at least statistically-significant values indicating on at least drift from initial calibrated values of each of the at least one sensor device; for each identified drifted sensor device, computing re-calibration updates, wherein the re-calibration updates adjust the initial calibrated values such that readings of the respective drifted sensor device fall within a range of expected values; and transmitting the re-calibration updates to the respective drifted sensor device, wherein the respective drifted sensor device upon receiving the re-calibration updates is configured to update its calibration parameters.

Certain embodiments disclosed herein also include a system for remote calibration of an air-quality sensor device. The system comprises: a processing circuitry; and a memory, the memory containing instructions that, when executed by the processing circuitry, configure the system to: receive sensor data from at least one sensor device; analyze the received sensor data to identify at least statistically-significant values indicating on at least drift from initial calibrated values of each of the at least one sensor device; for each identified drifted sensor device, compute re-calibration updates, wherein the re-calibration updates adjust the initial calibrated values such that readings of the respective drifted sensor device fall within a range of expected values; and transmit the re-calibration updates to the respective drifted sensor device, wherein the respective drifted sensor device upon receiving the re-calibration updates is configured to update its calibration parameters.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

Figure 1:
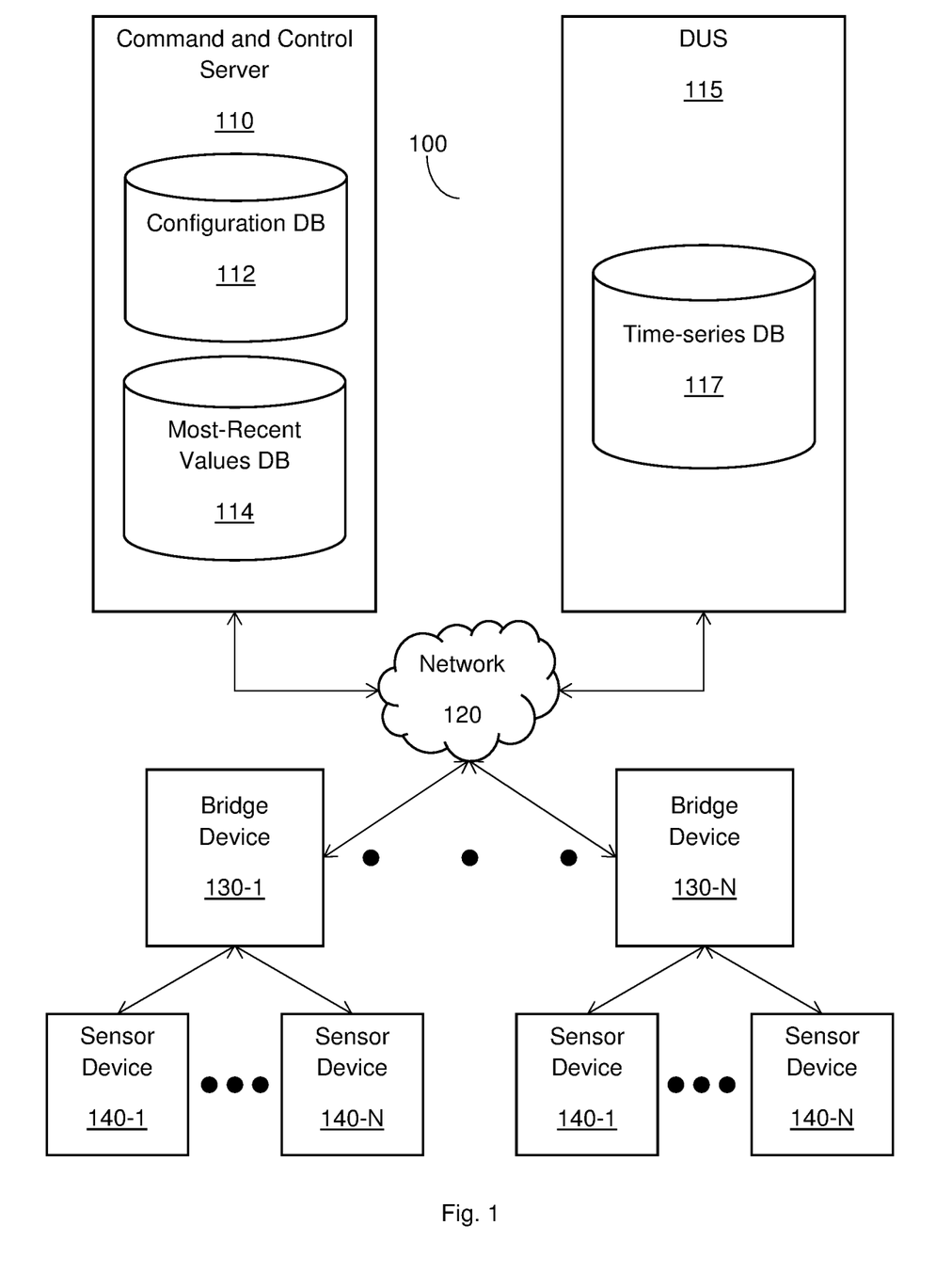
FIG. 1 is a network diagram utilized to describe a system for management of building air quality assurance, comfort wellness, and energy management, according to an embodiment.

FIG. 1 is an example network system 100 depicting the various embodiments for management of building air quality assurance, comfort, wellness, and energy management, according to an embodiment. A network system 100 may include one or more components such as, as examples and without limitation, a command and control server (CCS) 110, a data upload server (DUS) 115, a network 120, one or more bridge devices 130-1 through 130-N (hereinafter, "bridge device" 130 or "bridge devices" 130), as well as one or more sensor devices 140-1 through 140-N (hereinafter, "sensors" 140 or "sensor" 140). In an embodiment, a bridge device 130 is a building air quality assurance, comfort, or energy management device.

The CCS 110 is configured to provide for cloud-level administration of one or more bridge devices 130, sensor devices 140, and the like, as well as any combination thereof. The CCS 110 may be also configured to communicate with one or more components of the network system 100 via the network 120, according to the means described hereinbelow. The CCS 110 may include various processing, memory, and networking components, and the like, allowing the CCS 110 to execute instructions and provide data processing, including those methods or processes described hereinbelow. Further, the CCS 110 may be configured to include one or more databases, data repositories, or other, like, storage components, where the included storage components may be physical, virtual, or any combination thereof. The CCS may be configured to include, without limitation, a most recent values database 114, a configuration database 112, and the like, as well as any combination thereof, as described hereinbelow. The CCS 110 may be implemented as physical hardware, as software virtualizing physical hardware, or as a combination of physical and virtualized components. In an embodiment, the CCS 110 may be configured to operate as a data upload server (DUS) 115, as described hereinbelow. A detailed view of a CCS, according to an embodiment, is provided with respect to FIG. 6, below.

The most recent values database 114 provides storage for register data, as may be collected according to the processes described hereinbelow, organized by order of receipt. Registers may include data features describing, variously, device and component operating systems, device-specific data features, user-defined features, and the like. Register data may include data relating to the operating system or systems of various components of a network system 100.

In addition, register data may include data relating to the operation of various components of the sensor and bridge devices, describing component-specific data features, such as, as an example and without limitation, the firmware version of a specific sensor. Further, register data may include user register data, where user register data is data relevant to a user's custom purpose. As an example, user register data may include custom-generated instruction sets for personalizing sensor device data output formats. In addition, register data may include, without limitation, data relevant to device identification and manufacture, such as the firmware version of a given sensor device 140, the serial number of a given sensor device 140, lot and batch numbers of a given sensor device 140, and the like, as well as any combination thereof.

The configuration database 112 provides storage for system configuration instructions and collected data. Data which may be stored in the configuration database 112 includes, as examples and without limitation, sensor calibration data, building management system interface data, updated code images, various factory commands, DUS assignments, market and environmental data, register updates, device-specific commands, other, like, data, and any combination thereof.

The data upload server (DUS) 115, is a cloud-level server providing for collection and storage of data from one or more bridge devices 130, sensor devices 140, connected building management systems (not shown), and the like, as well as any combination thereof. The DUS 115 may be a resident server, located and operated on-location where the one or more bridge devices 130 and sensor devices 140 are deployed. Further, the DUS 115 may be a hosted server, located off-site and, in an embodiment, hosted by a platform configured to provide cloud computing, storage, and other, like, services, including, as examples and without limitation, Amazon® Web Services, Microsoft® Azure, and other, like, platforms.

The DUS 115 may include one or more storage or memory components, such as the time series database 117, and the like. The time series database 117 may be configured to store data received or collected according to the methods described hereinbelow, as well as other, like, methods. Data stored in the DUS 115, including data stored in the time series database 117, may be encrypted, unencrypted, or partially-encrypted. Further, stored data may be compressed to various degrees and may be stored to one or more physical partitions or other, like, separated storage allocations. The DUS 115, and any sub-component thereof, may be implemented as physical hardware, as software virtualizing physical hardware, or as a combination of physical and virtualized components. Further, the DUS 115 may be interconnected with the various components of the network system 100, via the network 120, according to the various means described hereinbelow.

The network 120 provides interconnectivity between the various components of the network system 100. The network 120 may be, but is not limited to, a wireless, cellular, or wired network, a local area network (LAN), a wide area network (WAN), a metro area network (MAN), the Internet, the worldwide web (WWW), similar networks, and any combination thereof. The network may be a full-physical network, including exclusively physical hardware, a fully-virtual network, including only simulated or otherwise virtualized components, or a hybrid physical-virtual network, including both physical and virtualized components. Further, the network 120 may be configured to encrypt data, both at rest and in motion, and to transmit encrypted, unencrypted, or partially-encrypted data.

The bridge devices 130 are devices configured to serve as intermediaries between the sensor devices 140 and the various components of the network system 100. The bridge devices 130 may be configured to, as examples and without limitation, collect data from various sensor devices 140, to upload or push instructions to the various sensor devices 140, to upload or push collected data to the various components of the network system 100, to collect, from the various components of the network system 100, various instructions, to collect data, independent of the various sensor devices 140, to execute instructions, and the like, as well as any combination thereof.

The bridge devices 130 may be configured to connect with the various components of the network system 100 via the network 120, according to the means described hereinabove. Further, the bridge devices 130 may be configured to connect with the various sensor devices 140 via wired or wireless means, or any combination thereof, such as those described hereinabove, via those protocols described with respect to the network 120, as well as other, like, protocols, or any combination thereof. In addition, the bridge devices 130 may be configured to encrypt data, both at rest and in motion, and to transmit data with varying degrees of encryption.

The bridge devices 130 may be configured to execute instructions and process data relevant to the various components of the system via connections to the various devices according to various pre-defined communication protocols, patterns, exchange systems, and the like, including via the network 120, as described hereinabove. An example implementation of a bridge device 130 is further disclosed in U.S. patent application Ser. No. 17/015,892 filed herewith, assigned to the common assignee, and the contents of which are hereby incorporated by reference.

The sensor devices 140 are devices configured to provide for collection of data pertinent to building air quality, comfort, wellness, and energy management. The sensor devices 140 may be include one or more sensors such as, as examples and without limitation, thermometers and gas detection and measurement sensors, hygrometers, and the like, as well as any combination thereof. Further, sensor devices 140 may be configured to collect data and to transmit collected data to the various components of the network system 100 via the bridge devices 130, to execute instructions received, via the bridge devices 130, from the various components of the network system 100, to execute other, like, functions, as well as any combination thereof. The sensor devices 140 may be configured to connect with the bridge devices 130 via those means described hereinabove. In a preferred embodiment, the sensor devices 140 and a bridge device 130 securely communicate over a wireless medium using an air-quality communication protocol. In an embodiment, the sensor devices 140 may be configured to connect directly with the network 120, via those means described herein, without connection to a bridge device 130. An example implementation of a sensor device 140 is further disclosed in U.S. patent application Ser. No. 17/015,918 filed herewith, assigned to the common assignee, and the contents of which are hereby incorporated by reference.

Figure 2:
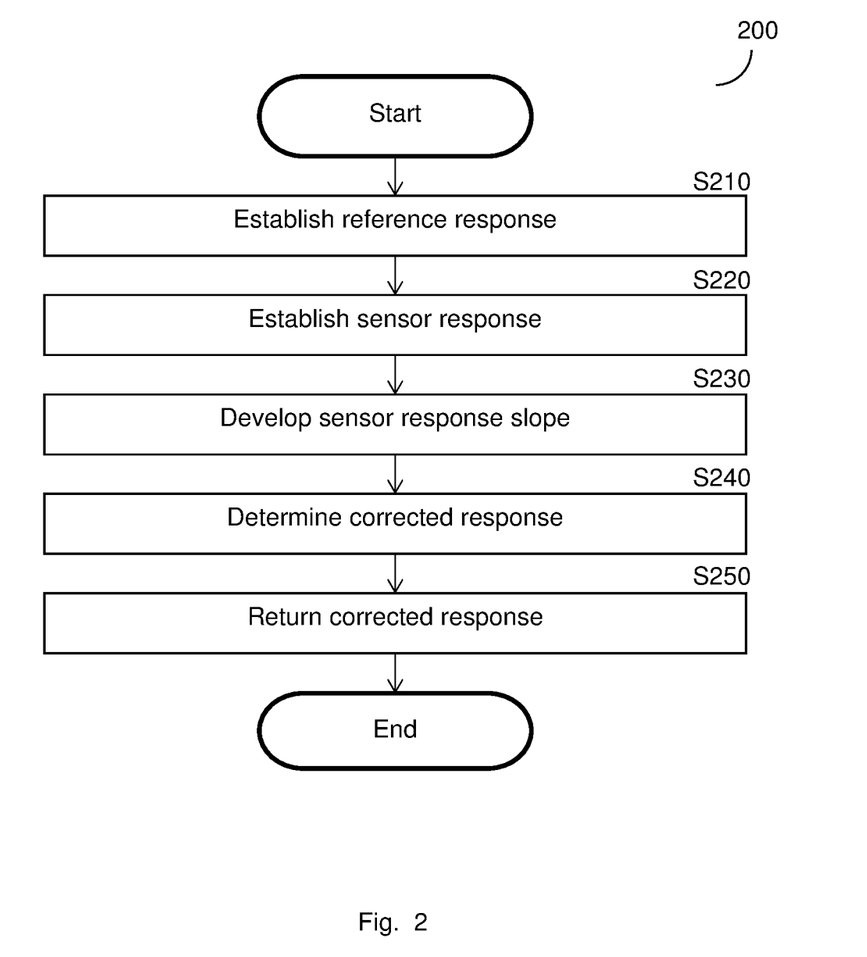
FIG. 2 is a flowchart depicting a method for sensor initial calibration, according to an embodiment.

FIG. 2 is an example flowchart 200 depicting a method for initial calibration of a sensor device 140, according to an embodiment. One or more of the steps described with respect to the method 200 for sensor initial calibration may be performed using a calibration device including, without limitation, the device described with respect to FIG. 4, below. The method described with respect to FIG. 2 may be executed by one or more components of a network system, such as the network system, 100, of FIG. 1, above, including, without limitation, the CCS 110, and the like, as well as any combination thereof.

At S210, reference responses are established. Reference responses are data outputs collected in response to environmental conditions, where such environmental conditions may be those conditions relevant to the collection of environmental data by a sensor device, including, without limitation, temperature, humidity, particulate and gas concentrations, light levels, other, like, conditions, and any combination thereof. Reference responses may be collected from one or more calibrated sources including, without limitation, test gasses, including ambient gas concentrations measured via a calibrated device, calibrated measurement devices, and the like, as well as any combination thereof.

Reference responses may be established, based on one or more environmental condition data points, according to one or more pre-defined or user-defined rules. Relevant environmental condition data may include, without limitation, building or space occupancy, known building ventilation settings, current system date or time, various outside references, such as weather reports, and the like, as well as other, like, condition data, and any combination thereof. Further, reference responses may be established based on one or more provided or collected data features including, without limitation, data features describing environmental conditions, as may be collected from one or more building management systems (BMSs), or various components or sub-components thereof.

As a first example, reference responses may be established, for a carbon dioxide sensor, where room occupancy is low and where ventilation is set to a level standard for the location, providing for collection of carbon dioxide sensor data at conditions approaching ambient conditions which have, for example, known concentrations of carbon dioxide ($CO_2$). Further, according to the same example, such ambient conditions may be validated by comparison with one or more factors, known to various components of a network system, such as the CCS, bridge, and sensor devices, of FIG. 1, above, and the like, where such factors may include, without limitation, calendar dates, such as holidays and weekends, other, like, data, and any combination thereof, providing for collection of reference values for ambient environmental conditions, where such reference values may be considered as reference values collected with respect to a known reference gas.

Further, as a second example, reference responses may be established for an ozone sensor with respect to a known building air-flushing schedule, providing for collection of reference responses to outside air entering the sample space during the air-flushing process, where such reference responses may be further confirmed by comparison with data collected by weather stations and air-monitoring stations.

In an additional example, collection of reference response data may be suspended where outside references, such as weather reports, indicate a high degree of smog or smoke in an area, providing for collection only of standard reference response data for application in establishing reference responses. Further, according to the same example, one or more network system components, such as the CCS, bridge, or sensor devices, and the like, as well as any combination thereof, of FIG. 1, above, may be configured to average multiple outside reference values and report a single, averaged outside reference value, as well as to filter outlying values and perform other, like, data analysis and filtering processes with regard to collected outside reference data.

In a further example, reference responses may be established based on reference response data provided by a BMS, providing for establishment of reference responses based on "authoritative" BMS-supplied reference values including, without limitation, temperature, relative humidity, and the like, as well as any combination thereof.

In an additional example, reference responses may be established conditionally based on the inclusion of one or more sensor types, such as barometric sensors, providing for establishing reference responses based on data collected from such sensors, such as by including an additional term in an absolute humidity reference response calculation.

Reference responses may be raw-data responses, such as measurements of voltage, current, resistance, and the like, as may be collected from calibrated sources in response to environmental conditions. Where reference responses are raw-data responses, such responses may be converted into measured values by application of one or more scaling factors, conversion algorithms, and the like, configured to represent raw-data responses in formats relevant to the various sensor types including, without limitation, temperatures, light levels, humidity values, particulate and gas concentrations, and the like. Further, reference responses may be established for one or more measurement points including, without limitation, high and low measurements, as well as other, like, points.

At S220, sensor responses are established. Sensor responses are data outputs collected from un-calibrated sensors in response to the same or similar environmental conditions described with respect to S210. Sensor responses may be established by the same means described with respect to S210, including by collection of raw-data responses, from one or more sensor devices. In addition, as described with respect to S210, raw-data responses may be subsequently converted into sensor-type measurement values such as, as examples and without limitation, temperatures, relative humidity values, light levels, gas and particulate concentrations, and the like. Further, sensor responses may be established with respect to one or more environmental conditions, including high and low measurements, as well as other, like, measurements. Further, sensor responses may be established for one or more sensors entering an inspection process, for one or more sensors included in finished devices, and the like, as well as any combination thereof.

At S230, sensor response slopes are developed. Sensor response slopes are measures of a sensor's reported measurement values, where sensor reported measurement values are represented as linear interpolations of non-linear functions, such as quadratic equations, measured with respect to the condition to which the sensor is exposed, such as, for example, a calibrated gas with a known concentration. Sensor response slopes may be developed according to the following equation:

$$M_{sense} = \frac{(S_{HR} - S_{LR})}{(A_H - A_L)}$$

In the above equation, where the sensor response is described as a linear approximation, the sensor response slope, $M_{sense}$, is given as the quotient of a numerator, representing a sensor value rise, divided by a denominator, representing a sensor value run, wherein the numerator is equal to the highest reported sensor value, given as $S_{HR}$, less the lowest reported sensor value, given as $S_{LR}$, and where the denominator is equal to the highest actual value, $A_H$, less the lowest actual value, $A_L$.

As an example, the linear sensor response slope for a temperature sensor may be determined by collecting two sensor measurements at known, respective room temperatures of sixty and fifty degrees. Where the sensor reports high and low values of sixty-five and forty-five degrees, respectively, the sensor response slope may be determined according to the above equation. According to the same example, the numerator applied to the above equation may be equal to twenty degrees, determined by subtracting the lowest reported sensor value of forty-five degrees from the highest reported sensor value of sixty-five degrees. Further, according to the same example, the denominator applied to the above equation may be equal to ten degrees, determined by subtracting the lowest actual value of fifty degrees from the highest actual value of sixty degrees. As a result, according to the same example, the sensor response slope may be equal to two, determined by dividing twenty degrees by ten degrees, as described hereinabove. According to the same example, where the sensor response slope is equal to two, such a value may indicate that the change in the sensor's response is double the actual change in the property or environmental condition detected by the sensor.

Further, S230 may include development of reference response slopes. Reference response slopes may be determined according to the equation described with respect to determination of sensor response slopes, with modifications included to address reference response highs and lows instead of sensor device response highs and lows. As described with respect to S210, reference response slope data may be collected from one or more calibrated sources.

At S240, corrected responses are determined. A corrected response is a sensor calibration correction configured to provide for calibration of a sensor device based on sensor and reference response slopes and established data, as described hereinabove. Corrected sensor responses may be determined according to the following equation:

$$\text{Sensor}_{corrected} = \left(\delta \text{Sensor}_{reported} * \frac{M_{reference}}{M_{sensor}}\right) + R_{LR}$$

According to the above equation, a sensor correction is equal to the sum of the reference device low reported measurement, $R_{LR}$, as established at S210, added to the product of the quotient of the reference response slope, $M_{reference}$, divided by the sensor response slope, $M_{sense}$, both as determined at S230, multiplied by the difference between sensor and reference reported values, or the offset, given as $\delta \text{Sensor}_{reported}$. The offset value is determined by subtracting the sensor low response value, determined at S220, from the reference low response value, determined at S210.

At S250, corrected responses are returned. Corrected responses, as determined at S240, as well as component parameter values, as described hereinabove, may be returned by one or more means including without limitation, storage to one or more sensor devices for calibration, by uploading and persisting corrected responses to one or more location for subsequent use and tracking, other, like, means, and any combination thereof. Further, corrected responses may be returned by display or presentation of sensor responses via one or more means including, without limitation, display through a screen or display included in a device, return as a print-out or other, like, format, and the like, as well as any combination thereof. In addition, according to an embodiment, returning corrected responses at S250 may further include labeling of individual sensors with identifying information including, without limitation, serial numbers, batch numbers, lot numbers, and the like, as well as any combination thereof, and returning such identifying information as described hereinabove. Stored corrected responses, corrected response parameter values, and sensor serial, lot, and batch numbers, may be stored to one or more memory or storage components, including the memory or storage components described with respect to the network system, 100, of FIG. 1, above, providing for subsequent analysis of such data for purposes including, without limitation, execution of one or more over-the-air (OTA) re-calibration methods, such as that described with respect to FIG. 5, below. Further, stored corrected responses, and the various component parameters thereof, may be, at the execution of S250, correlated to a given sensor device and stored to one or more memory components, wherein such memory components may be communicably connected with the given sensor device to which the stored corrected responses are correlated.

In addition, returning corrected responses at S250 may include returning multiple corrected responses for a single sensor device. Multiple corrected responses may be generated, according to the methods described hereinabove, for a single sensor device based on multiple distinct correction response parameters, such as slopes and offsets, as described hereinabove. Multiple correction response parameters may be collected according to the methods described hereinabove, across multiple iterations of a sensor initial calibration process. Where multiple calibration response parameters are collected, the collected response parameters may be stored and applied to the generation of multiple corrected responses, providing for the generation of multiple corrected responses for the same sensor device, as may be applicable to the identification of one or more ideal or preferred corrected responses.

It should be noted that the initial calibration is performed on any detector or sensor component in the sensor device. Such detectors may include, without limitation, a carbon dioxide ($CO_2$) detector, a particulate matter detector, a formaldehyde ($CH_2O$) detector, a carbon monoxide (CO) detector, a relative humidity detector, an ozone (O3) detector, a wide-band total volatile organic compound (TVOC) detector, a light level detector, a narrow-band or high-sensitivity TVOC detector, and the like.

Figure 3:
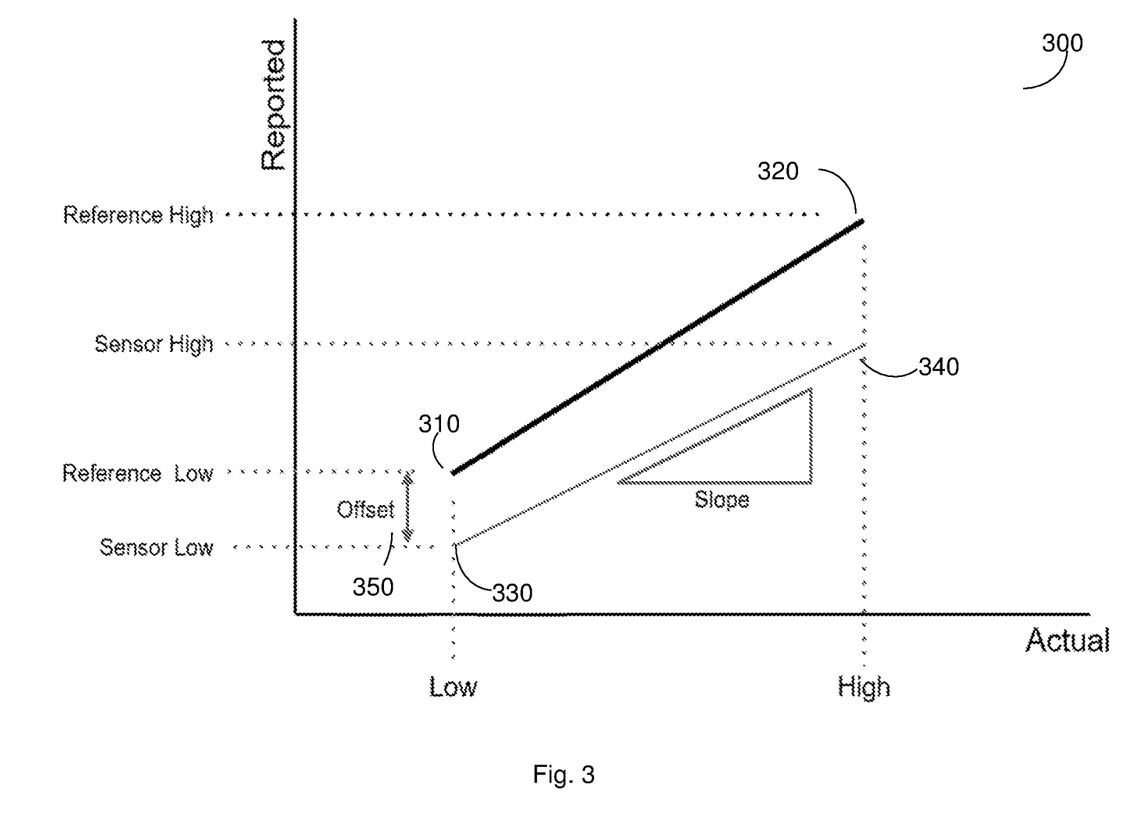
FIG. 3 is an illustration depicting sensor and reference responses, according to an embodiment.

FIG. 3 is an illustration 300 depicting sensor and reference responses, according to an embodiment. The illustration 300 provides a visual depiction of the relationships between the quantities noted with respect to FIG. 3, above. The illustration 300 includes a reported reference low value 310, a reported reference high value 320, a reported sensor low value 330, a reported sensor high value 340, and an offset value 350.

The reported reference low value 310 is a value reported by a calibrated source, as described hereinabove, for an environmental condition with a known low value, such as a minimum temperature in a temperature-testing schedule. Further, the reported reference low value 310 may be the lowest value which the given calibrated source can measure and report. The reported reference high value 320 is a value reported by a calibrated source, also as described hereinabove, for an environmental condition with a known high value, such as a maximum temperature in a temperature-testing schedule. In addition, the reported reference high value 320 may be the highest value which the given sensor can measure and report.

The reported sensor low value 330 is a value reported by an uncalibrated sensor, such as a sensor undergoing a calibration process as described with respect to FIG. 3, above, for an environmental condition with a known low value. Further, the reported sensor low value 330 may be the lowest value which the given sensor can measure and report. Similarly, the reported sensor high value 340 is a value reported by an uncalibrated sensor for an environmental condition with a known high value. In addition, the reported sensor high value 340 may be the highest value which the given sensor can measure and report. The offset value 350 is a value describing the difference between the reported reference low value 310 and the reported sensor low value 330.

Figure 4:
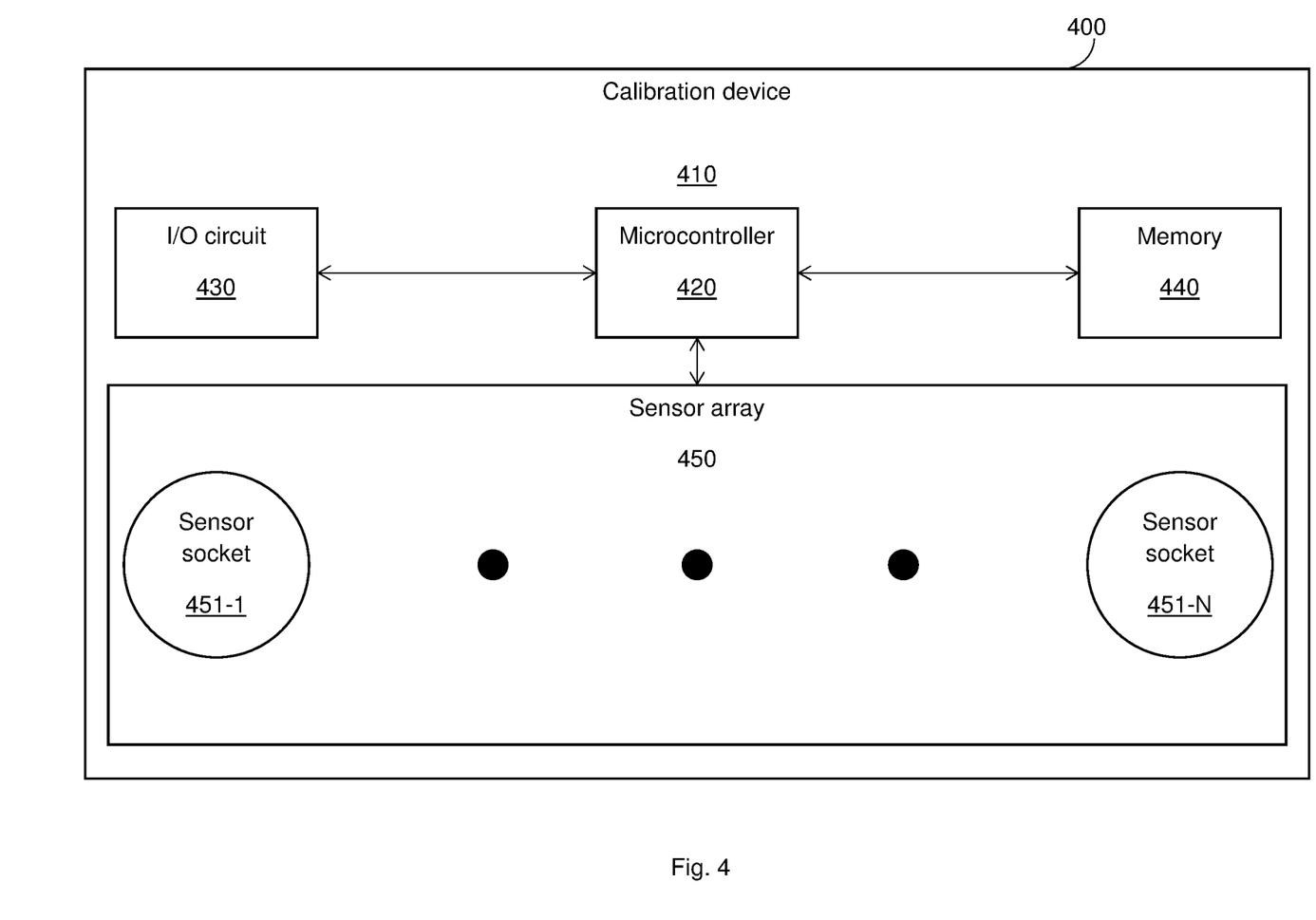
FIG. 4 is an illustration depicting a device for initial calibration of sensors, according to an embodiment.

FIG. 4 is an illustration depicting a device for initial calibration of sensors, according to an embodiment. the calibration device 410 is a device providing for low-cost means for validating, measuring, or both validating and measuring sensor offset and slope parameters, as described hereinabove. Further, the calibration device 410 may be configured to provide means for retaining sensor samples in states wherein periodic measurements may be automated. Operation of a calibration device may include, in addition to the method described with respect to FIG. 2, above, sensor sampling across intervals corresponding to sensor production batches or lots. The calibration device may include a microcontroller 420, an input/output (I/O) circuit 430, a memory 440, a sensor array 450, and a plurality of sensor sockets 451-1 through 451-N (hereinafter, "sensor socket" or "sensor sockets"). In an embodiment, a calibration device 410 may further include one or more removeable memory devices (not shown), configured to store various calibration parameters, as described herein, and further configured to be disconnected from a calibration device 410 and connected to other devices, including sensor devices, for purposes including, without limitation, transferring data between the calibration device 410 and other devices, for other, like, purposes, and any combination thereof.

The sensor array 450 includes sensor sockets 451, configured to connect with one or more sensor or detector components, as may be include in a sensor device, such as, as examples and without limitation, carbon dioxide ($CO_2$) detectors, particulate matter detectors, formaldehyde ($CH_2O$) detectors, carbon monoxide (CO) detectors, relative humidity detectors, ozone ($O_3$) detectors, wide-band total volatile organic compound (TVOC) detectors, light level detectors, narrow-band or high-sensitivity TVOC detectors, and the like.

In an embodiment, the calibration device 410 may be configured to provide one or more sensor device burn-in functionalities. A sensor device burn-in functionality may be, without limitation, a calibration device 410 mode of operation configured to, as examples and without limitation, identify defective sensor devices, normalize sensor device operations from a production state to an operation state, and the like, as well as any combination thereof. Where a calibration device 410 is configured to provide burn-in functionality for identifying defective sensor devices, the calibration device 410 may be configured to energize one or more sensor devices, connected through the sensor sockets 451, within pre-defined operating power levels, and to maintain sensor device energization for a given period of time, providing for identification of defective sensor devices by detection of devices which "burn-out" or fail before reaching a predetermined burn-in period length.

Further, where a calibration device 410 is configured to provide burn-in functionality for normalizing sensor operations, the calibration device 410 may be configured to provide, to the connected sensor devices, power at one or more levels, providing for adjustment of sensor device operations from as-manufactured states to operational states by "aging" the energized sensor devices, including adjustment of sensor device readings, for sensors in the same lot, toward a median value. As an example of a normalizing functionality, sensors which mis-report environmental conditions when first manufactured, by either under- or over-reporting, may be "aged" to an operational state by energizing the sensor devices until sensor device readings for multiple devices converge at a median value. In addition, a normalizing functionality may include an additional burn-in cycle following the aging of sensor devices to the described median value, providing for the adjustment of the described median value to a value representing a median un-calibrated sensor reading, based on a provided environmental condition.

A calibration device 410 may be configured to provide for calibration of one or more types of sensor devices. A calibration device 410 may include, in addition to sensor sockets 451, one or more means for connection with various sensor devices including, without limitation, pin-type connectors, universal serial bus (USB) connectors, pure-signal electrical connectors, such as "alligator clips," and the like, as well as any combination thereof.

A calibration device 410 may be configured to provide environmental testing conditions, exposing connected sensors to one or more conditions including, without limitation, various temperatures, air pressures, relative humidity levels, gas and particulate exposures, light levels, and the like, as well as any combination thereof. As examples, and without limitation, a calibration device 410 may be configured to calibrate sensors including temperature sensors, relative humidity sensors, light level sensors, air pressure sensors, particulate and gas detectors, and the like, as well as any combination thereof.

The microcontroller 420 is a processing circuitry configured to execute instructions, including instructions relevant to those processes described herein, and other, like, processes, and may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The I/O circuit 430 is a hardware component configured to provide connectivity between the calibration device and various other devices and systems including, without limitation, the network system, 100, of FIG. 1, above, and various components thereof. The I/O unit may be configured to provide wireless connectivity by means including, without limitation, ethernet, serial I/O, universal serial bus (USB), and the like, via wireless means including, without limitation, Bluetooth, infrared, Wi-Fi, and the like, as well as any combination of wired and wireless means.

The memory 440 is a component providing for temporary, semi-permanent, or permanent storage of one or more data features related to the operation of the calibration device 410 including, without limitation, sensor and reference response values, sensor corrections, short-term values applicable to execution of various calculations, other, like, data features, and any combination thereof. The memory 440 may be volatile (e.g., random access memory, etc.), non-volatile (e.g., read only memory, flash memory, etc.), or a combination thereof.

In one configuration, software for implementing one or more embodiments disclosed herein may be stored in a storage (not shown). In another configuration, the memory 440 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the microcontroller 420, cause the microcontroller 420 to perform the various processes described herein.

Figure 5:
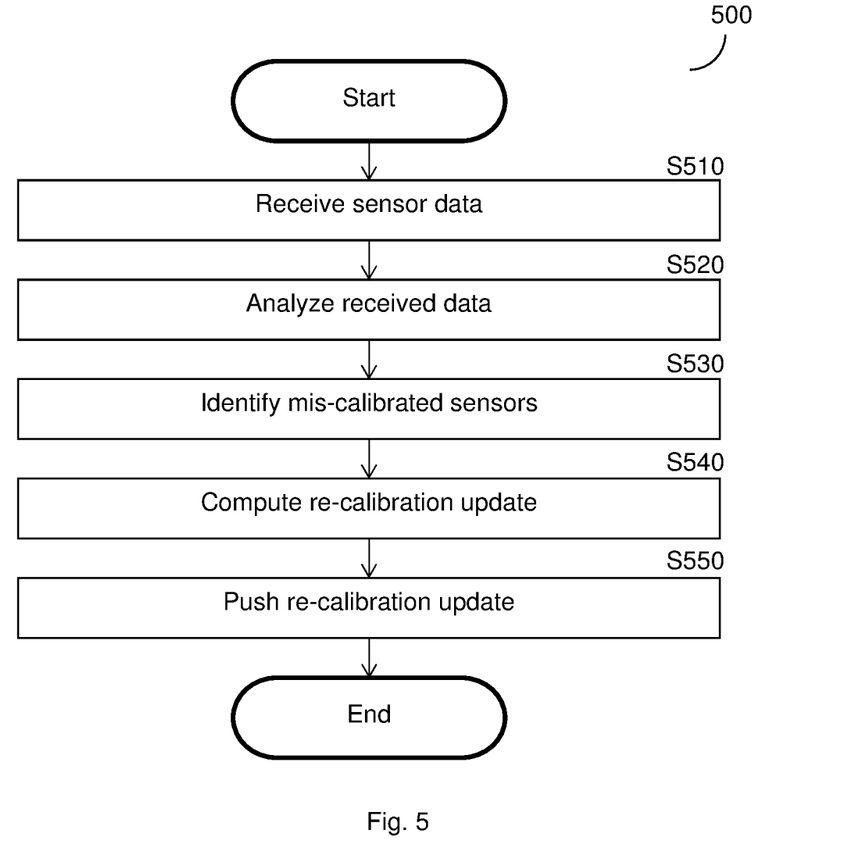
FIG. 5 is a flowchart depicting a method for over-the-air (OTA) sensor re-calibration, according to an embodiment.

FIG. 5 is an example flowchart 500 depicting a method for calibration of an air-quality sensor device, according to an embodiment. The method 500, in an embodiment, may be executed by a remote server, such as a CCS (e.g., CSS 110, FIG. 1). In an embodiment, the method 500 includes re-calibration of the initial calibration parameters set for the sensor device at the factor. The re-calibrated parameters' values are sent to the sensor device over-the-air (OTA). The calibration method described with respect to FIG. 5 may be applicable to calibration of one or more sensors or detectors, as may be included in a sensor device, such as, as examples and without limitation, carbon dioxide ($CO_2$) detectors, particulate matter detectors, formaldehyde ($CH_2O$) detectors, carbon monoxide (CO) detectors, relative humidity detectors, ozone ($O_3$) detectors, wide-band total volatile organic compound (TVOC) detectors, light level detectors, narrow-band or high-sensitivity TVOC detectors, and the like.

At S510, sensor data is received from one or more sensor devices. For each sensor, the data includes metadata describing sensor device's attributes, personalization requests, as well as data features related the sensor's recorded sensor readings. Sensor metadata may include, without limitation, sensor device, serial number, lot, batch number, location, and type. The metadata may further include data features collected by one or more sensor devices, and the like, as well as any combination thereof. Data features collected by one or more sensor devices may include instantaneous and time-delayed sensor readings, charts, graphs, tables, and other, like, data features describing sensor trends, patterns, and the like, in environmental readings, various data registers relevant to collected sensor data, other, like, data features, and any combination thereof.

A personalization request may be a persistent sensor value offset, providing of overriding adjustment of one or more collected sensor measurements. A personalization request may be generated by a user, such as through a sensor device interface, automatically, including by one or more BMS systems or components thereof, and the like, as well as any combination thereof. As an example, a personalization request may include a persistent offset, set by a user through a sensor device, providing for sensor under-reporting by specification of a "minus five degrees" offset for a temperature sensor. Sensor data may be received from one or more sensor or bridge devices including, without limitation, the sensor devices, 140, and bridge devices, 130, of FIG. 1, above.

At S520, the received sensor data is analyzed. Received data may be analyzed to identify one or more patterns, trends, and statistically-significant values in the received data, and the like. Patterns, trends, and the like, as may be identified at S520, may include periodic fluctuations of sensor reading data, such as temperature cycles occurring over the course of a day, long-term sensor drift patterns, such as increases in sensor reading values over a span of months, despite no change in a sensor's environmental conditions, other, like, patterns and trends, and any combination thereof.

In an example embodiment, statistically-significant values may include, without limitation, minimum, maximum, mean, and median sensor values, as well as various distributions and analyses thereof, and the like, as well as any combination thereof. Received data may be analyzed by application of one or more algorithms, methods, processes, and the like, configured to identify trends, patterns, and statistically-significant values in received sensor data.

In an additional embodiment, analysis at S520 may further include analysis configured to identify long-term and short-term sensor drift. Sensor drift describes the tendency of a sensor device to, with time, report values which differ from values expected from a properly-calibrated sensor. Sensor drift may include a time-dependency, whereby sensor reported values may differ from expected values to a greater degree with increasing time separation from a most-recent calibration update. Sensor drift may be short-term drift, applicable to drift phenomena across relatively short time periods, such as minutes, hours, or days. Further, sensor drift may be long-term drift, applicable to drift phenomena across longer time periods, such as weeks, months, and years. It may be understood that the respective time periods described with respect to short-term and long-term drift are provided as examples, and that other, like, time periods may be applicable without loss of generality or departure from the scope of the disclosure.

Short-term drift and long-term drift may be identified, during analysis at S520, by analysis of data derived from one or more sensor readings including, without limitation, analysis of sensor reading distributions for similar devices, as well as tendencies of such distributions to "drift" away from an initial median over time. Sensor readings may be analyzed to determine current and historical reported values, trends in reported values over time, and the like, as well as any combination thereof. Drift may be identified by correlation of current and historical reported values, and trends relative thereto, with reference values obtained by one or more means including, as examples and without limitation, long-term sampling of control sensors from the same lot or batch, retained at the point of calibration or manufacture to provide reference values for drift detection, sampling of other, deployed, sensors of the same lot or batch, comparison with expectation values derived based on known sensor properties and drift patterns, and the like, as well as any combination thereof. Further, identification of drift may include comparison of sensor readings with one or more threshold values, wherein the threshold values may be determined based on the reference values described hereinabove, including threshold values determined by application of one or more algorithms, methods, or the like to the various reference values. In addition, identification of drift may include identification of drift based on comparison of sensor drift patterns with one or more threshold patterns or values, wherein such threshold patterns or values may be determined according to methods similar or identical to those described hereinabove. Where drift is identified at S520, identification of mis-calibrated sensors at S530 may include identification of sensors reporting drift values, and computation of re-calibration updates at S540 may include computation of updates including corrections to adjust for identified drift.

At S530, mis-calibrated sensors are identified. Mis-calibrated sensors are sensors reporting data values which differ from expected reporting values by amounts exceeding one or more pre-defined thresholds. Mis-calibrated sensors may be identified by determination of, based on the results of the analysis performed at S520 and without limitation, sensors reporting values above or below expected values by amounts exceeding given thresholds, sensors regularly reporting anomalous values, such as weekly temperature spikes exceeding predefined thresholds, sensors reporting values which differ, by more than a predefined threshold, from values reported by co-located sensors of the same type, other, like, determinations, and any combination thereof. In addition, sensors may be identified as mis-calibrated where a sensor's current or historical drift, or drift patterns, exceeds pre-determined thresholds. Further, in an embodiment, sensor devices may be identified as mis-calibrated where one or more sensor devices have not been the targets of a re-calibration process, such as that defined with respect to FIG. 5, for more than a predefined time period, such as sensors which have not been re-calibrated within the previous calendar month. In an additional embodiment, sensors may be manually identified as mis-calibrated by an administrator or other user, including manual identifications through various sensor devices, bridge devices, CCSs, and other, like, components of a network system, such as the network system, 100, of FIG. 1, above.

At S540, re-calibration updates are computed. Re-calibration updates are updates configured to calibrate a sensor device such that the sensor device's reported readings fall within a range of expected values. Such a range of expected values is based on a reference reported value, to which is applied a pre-defined statistical deviation, providing for a range of expected reading values. Re-calibration updates may be transmitted in a form scripts, firmware updates, and other, like, modifications of sensor device software or application configured to provide for over-the-air (OTA) sensor device calibration.

Re-calibration updates may include updates configured to adjust the initial calibration data, such as the offset, slope, and other, like, parameters of a sensor device's corrected response, as described with respect to FIG. 2, above. Further, re-calibration updates may include updates configured based on sensor drift value, as determined based on data analyzed at S320, including updates configured to subtract such a sensor drift value from a current sensor reading value.

Computation of re-calibration updates may include identification of sensor drift for one or more sensors of the same lot, batch, type, and the like. Sensor lots, batches, and the like, may be identified based on one or more lot or batch identifiers, such as those generated as described with respect to FIG. 2, above. Identification of lot or batch drift may include comparison of average or median values for all sensors within a given lot or batch with one or more reference values, as described hereinabove, to identify one or more lots, batches, or other, like, groups of sensors which include sensors reporting anomalous environmental reading data. Where computing of re-calibration updates includes such lot or batch analyses, re-calibration update computation may further include computation of one or more updates, as described hereinabove, by automatic generation of scripts, firmware updates, and the like, targeted to specific sensor batches, lots, or serial numbers, and configured to update some or all of the sensors in a given lot or batch to report readings consistent with expected values derived from reference data, as described hereinabove.

Further, computation of re-calibration updates at S540 may include identification of one or more sensor devices to be excluded from re-calibration or to receive individual, one-off re-calibration updates. Sensor devices may be identified as excluded from re-calibration or subject to one-off updating based on one or more factors including, without limitation, sensor device location, sensor device ambient conditions, such as may be applicable to sensor devices placed in locations for which, in normal conditions, a sensor may report a value which would be considered anomalous, other, like, factors, and any combination thereof.

In addition, sensor devices may be identified as excluded from re-calibration or subject to one-off updating based on one or more conditional triggers, including by delaying a prepared re-calibration update until a point at which a room or space is unoccupied, by preparing a one-off update when a room is unoccupied, despite other update schedules or triggers, by preparing a one-off update including an offset different than that applied to a device of the same type in a different location, other, like, location and occupancy-related conditions, and any combination thereof. Further, sensor devices may be identified as subject to one-off updating based on one or more signals received from various components of a network system, and various systems connected therewith, including, without limitation, a BMS. Where a sensor device is identified as subject to one-off updating based on signals received from a BMS, including signals specifying that one or more BMS purge or reset processes are in progress, S540 may include computation of a one-off update for the identified sensor device or devices, despite other update schedules, update triggers, and the like. Where a sensor device is identified as being subject to a one-off re-calibration update, computation of re-calibration updates at S540 may include computation of re-calibration updates configured to provide for special re-calibration of a sensor device to provide for adjusted expected reading values.

In an embodiment, computation of re-calibration updates at S540 may include computation of updates based on manually-supplied re-calibration data. Manually-supplied re-calibration data may be collected from one or more sources including, without limitation, user input components, such as touchscreens, included in sensor devices, network controllers, such as the CCS 110, of FIG. 1, above, other, like, sources, and any combination thereof. Computation of updates based on manually-supplied re-calibration data may include, without limitation, generation of one or more corrected responses, as described hereinabove, based on user-specified or administrator-specified offset values, slope values, other, like, parameter values, and any combination thereof. Further, computation of updates based on manually-supplied re-calibration data may include computation of updates targeting specific, specified devices, computation of updates applicable according to various schedules or triggers specified by a user or administrator, and the like, as well as any combination thereof. In addition, where computation of updates is based on manually-supplied re-calibration data, computation at S540 may include computation of one or more updates, computed as described, for other, like sensor devices, as well as automatic restriction or rejection of updates based on manually-supplied data, where such data is determined, according to one or more pre-defined rules, to be improper or invalid. Where S540 includes computation of updates based on manually-supplied re-calibration data, S540 may be executed at any point prior to the execution of S550, including concurrently with, or to the exclusion of, S510, S520, or S530, without loss of generality or departure from the scope of the disclosure.

At S550, re-calibration updates are pushed. Pushing re-calibration updates may include execution, by a CCS or other, like device, one or more commands or instructions configured to send, to one or more bridge device, sensor devices, or both, re-calibration updates prepared at S540. Further, the commands or instructions executed at S540 may be configured to execute, in a target sensor or bridge device, one or more processes for updating device firmware, device operating code, and the like, providing for time-of-push updates to bridge and sensor device calibration parameters. Further, in an embodiment, pushing re-calibration updates at S550 may include, without limitation, manual entry of updated calibration parameters, such as calibration slopes or offsets, by an administrator or other user, through one or more components of a network system, such as bridge devices, sensor devices, and the like.

In an additional embodiment, re-calibration updates may be stored and pushed in response to one or more push-trigger conditions including, as examples and without limitation, one or more pre-defined or user-defined push delay waiting periods, one or more user-defined or pre-defined calendars or schedules, one or more update content triggers, as may be triggered where an update includes or excludes a specified value, one or more user or administrator push commands, and the like, as well as any combination thereof. As an example, according to the same embodiment, a re-calibration update push-trigger may be configured to provide for pushing updates where a system date or time falls between two predetermined dates or times, and where the contents of a register included in the update includes a given value.

Further, pushing re-calibration updates at S550 may include creation and storage of one or more re-calibration records. Re-calibration records may be data features describing the various re-calibration updates pushed at S550. Re-calibration records may include, without limitation, re-calibration update values, such as updated slopes, offsets, and the like, target device serial, lot, and batch numbers, target device locations, re-calibration update date and time, re-calibration update status, such as whether the update was successfully pushed, other, like, data, and any combination thereof. Re-calibration records created at S550 may be stored to one or more memory or storage components including, without limitation, those memory or storage components or sub-components of the network system, 100, of FIG. 1, above, and the like, as well as any combination thereof, providing for subsequent re-calibration update auditing and lot-tracing. Re-calibration records may be created or stored on a per-update basis, relevant to multiple devices re-calibrated by the same update, a per-unit basis, relevant to individual devices, other, like, bases, and any combination thereof.

Figure 6:
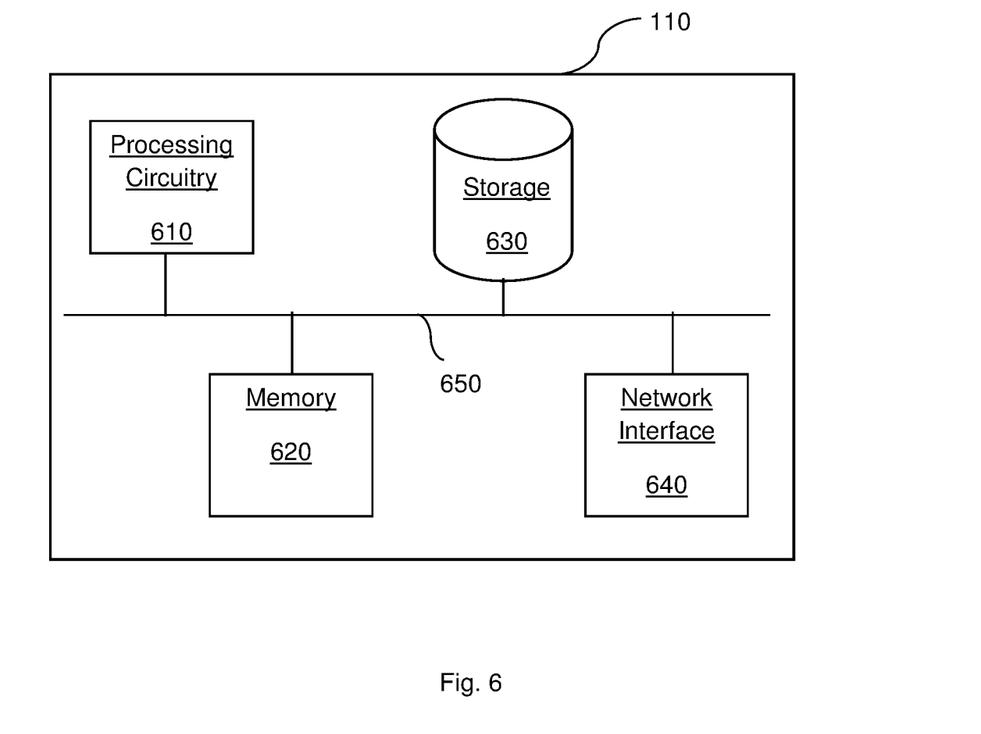
FIG. 6 is an example schematic diagram of a command and control server (CCS), according to an embodiment.

FIG. 6 is an example schematic diagram of a command and control server (CCS) 110, according to an embodiment. The CCS 110 includes a processing circuitry 610 coupled to a memory 620, a storage 630, and a network interface 640. In an embodiment, the components of the CCS 110 may be communicatively connected via a bus 650.

The processing circuitry 610 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 620 may be volatile (e.g., random access memory, etc.), non-volatile (e.g., read only memory, flash memory, etc.), or a combination thereof.

In one configuration, software for implementing one or more embodiments disclosed herein may be stored in the storage 630. In another configuration, the memory 620 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 610, cause the processing circuitry 610 to perform the various processes described herein.

The storage 630 may be magnetic storage, optical storage, and the like, and may be realized, for example, as flash memory or another memory technology, compact disk-read only memory (CD-ROM), Digital Versatile Disks (DVDs), or any other medium which can be used to store the desired information.

The network interface 640 allows the CCS 110 to communicate with the various components, devices, and systems described herein for calibration of building air quality assurance devices, as well as other, like, purposes.

It should be understood that the embodiments described herein are not limited to the specific architecture illustrated in FIG. 6, and other architectures may be equally used without departing from the scope of the disclosed embodiments.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other sensor units may be connected to the computer platform such as an additional data storage unit and a printing unit. Furthermore, a non-transitory computer readable medium is any computer readable medium except for a transitory propagating signal.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A method for remote calibration of an air-quality sensor device, comprising:
   receiving sensor data from at least one sensor device, each of the at least one sensor device being of a same type;
   analyzing the received sensor data to identify at least statistically-significant values indicating at least drift from initial calibrated values of each of the at least one sensor device;
   for each identified drifted sensor device, computing re-calibration updates, wherein the re-calibration updates adjust the initial calibrated values such that readings of the respective drifted sensor device fall within a range of expected values; and
   transmitting the re-calibration updates to the respective drifted sensor device, wherein the respective drifted sensor device upon receiving the re-calibration updates is configured to update its calibration parameters.

2. The method of claim 1, wherein the sensor data includes metadata, a personalization request, and data features.

3. The method of claim 2, wherein the sensor data includes instantaneous and time-delayed sensor readings of each of the at least one sensor, wherein the sensor readings are collected in response to environmental conditions monitored by a sensor device.

4. The method of claim 2, wherein the personalization request includes at least a persistent sensor value offset.

5. The method of claim 1, wherein analyzing the received sensor data to identify the at least statistically-significant values further comprises:
   correlating sensor readings received from at least two sensor devices to determine at least long-term sensor drift patterns and short-term sensor drift patterns.

6. The method of claim 5, wherein identifying the at least one drifted sensor device further comprises:
   comparing sensor readings of a sensor device to a pre-defined threshold; and
   determining the sensor device as a drifted sensor when sensor exceeds the pre-defined threshold.

7. The method of claim 6, wherein comparing the sensor readings further comprises:
   comparing the long-term sensor drift patterns and short-term sensor drift patterns to the pre-defined threshold.

8. The method of claim 1, wherein the initial calibrated values include at least a slope value and an offset value initially calibrated for each sensor device.

9. The method of claim 1, wherein transmitting the re-calibration updates further comprises:
   transmitting the re-calibration updates as over-the-air (OTA) provisioning, wherein re-calibration updates are in form of any one of: meta-data, script, firmware, and any operating code.

10. The method of claim 1, wherein the method is performed by a remote server remotely connected to the at least one sensor device.

11. The method of claim 1, wherein the re-calibration updates are computed for each identified drifted sensor device based on indicated drift from its initial calibrated values.

12. The method of claim 1, wherein the re-calibration updates are computed for each identified drifted sensor device based on a one of lot or batch to which the each identified drifted sensor belongs.

13. A non-transitory computer readable medium having stored thereon instructions for causing a processing circuitry to execute a process for remote calibration of an air-quality sensor device, the process comprising:
   receiving sensor data from at least one sensor device, each of the at least one sensor device being of a same type;
   analyzing the received sensor data to identify at least statistically-significant values indicating at least drift from initial calibrated values of each of the at least one sensor device;
   for each identified drifted sensor device, computing re-calibration updates, wherein the re-calibration updates adjust the initial calibrated values such that readings of the respective drifted sensor device fall within a range of expected values; and
   transmitting the re-calibration updates to the respective drifted sensor device, wherein the respective drifted sensor device upon receiving the re-calibration updates is configured to update its calibration parameters.

14. A system for remote calibration of an air-quality sensor device, comprising:
   a processing circuitry; and
   a memory, the memory containing instructions that, when executed by the processing circuitry, configure the system to:
   receive sensor data from at least one sensor device, each of the at least one sensor device being of a same type;
   analyze the received sensor data to identify at least statistically-significant values indicating at least drift from initial calibrated values of each of the at least one sensor device;
   for each identified drifted sensor device, compute re-calibration updates, wherein the re-calibration updates adjust the initial calibrated values such that readings of the respective drifted sensor device fall within a range of expected values; and
   transmit the re-calibration updates to the respective drifted sensor device, wherein the respective drifted sensor device upon receiving the re-calibration updates is configured to update its calibration parameters.

15. The system of claim 14, wherein the sensor data includes metadata, a personalization request, and data features.

16. The system of claim 15, wherein the sensor data includes instantaneous and time-delayed sensor readings of each of the at least one sensor, wherein the sensor readings are collected in response to environmental conditions monitored by a sensor device.

17. The system of claim 15, wherein the personalization request includes at least a persistent sensor value offset.

18. The system of claim 14, wherein the system is further configured to:
   correlate sensor readings received from at least two sensor devices to determine at least long-term sensor drift patterns and short-term sensor drift patterns.

19. The system of claim 18, wherein the system is further configured to:
   compare sensor readings of a sensor device to a pre-defined threshold; and
   determine the sensor device as a drifted sensor when sensor exceeds the pre-defined threshold.

20. The system of claim 19, wherein the system is further configured to:
   compare the long-term sensor drift patterns and short-term sensor drift patterns to the pre-defined threshold.

21. The system of claim 14, wherein the initial calibrated values include at least a slope value and an offset value initially calibrated for each sensor device.

22. The system of claim 14, wherein the system is further configured to:
    transmit the re-calibration updates as over-the-air (OTA) provisioning, wherein re-calibration updates are in form of any one of: meta-data, script, firmware, any operating code.

23. The system of claim 14, wherein the memory contains instructions which, when executed by a remote server remotely connected to the at least one sensor device, configure the remote server to:
    receive sensor data from at least one sensor device;
    analyze the received sensor data to identify at least statistically-significant values indicating on at least drift from initial calibrated values of each of the at least one sensor device;
    for each identified drifted sensor device, compute re-calibration updates, wherein the re-calibration updates adjust the initial calibrated values such that readings of the respective drifted sensor device fall within a range of expected values; and
    transmit the re-calibration updates to the respective drifted sensor device, wherein the respective drifted sensor device upon receiving the re-calibration updates is configured to update its calibration parameters.

24. The system of claim 14, wherein the re-calibration updates are computed for each identified drifted sensor device based on indicated drift from its initial calibrated values.

25. The system of claim 14, wherein the re-calibration updates are computed for each identified drifted sensor device based on a one of lot or batch to which the each identified drifted sensor belongs.

* * * * *